(12) United States Patent
Parys

(10) Patent No.: US 9,649,130 B2
(45) Date of Patent: May 16, 2017

(54) UTERINE MANIPULATORS AND RELATED COMPONENTS AND METHODS

(71) Applicant: CooperSurgical, Inc., Trumbull, CT (US)

(72) Inventor: James R. Parys, Wallingford, CT (US)

(73) Assignee: CooperSurgical, Inc., Trumbull, CT (US)

( * ) Notice: Subject to any disclaimer, the term of this patent is extended or adjusted under 35 U.S.C. 154(b) by 229 days.

(21) Appl. No.: 14/510,265

(22) Filed: Oct. 9, 2014

(65) Prior Publication Data

US 2016/0100862 A1    Apr. 14, 2016

(51) Int. Cl.
| | | |
|---|---|---|
| A61B 17/42 | (2006.01) |
| A61B 90/30 | (2016.01) |
| A61B 90/00 | (2016.01) |
| A61B 17/00 | (2006.01) |
| A61B 17/32 | (2006.01) |
| A61B 17/34 | (2006.01) |

(52) U.S. Cl.
CPC .......... *A61B 17/4241* (2013.01); *A61B 90/30* (2016.02); *A61B 90/39* (2016.02); *A61B 2017/00557* (2013.01); *A61B 2017/320052* (2013.01); *A61B 2017/347* (2013.01); *A61B 2017/4225* (2013.01)

(58) Field of Classification Search
CPC ................ A61B 17/42–17/48; A61B 1/32
See application file for complete search history.

(56) References Cited

U.S. PATENT DOCUMENTS

| | | | |
|---|---|---|---|
| 1,856,295 A | 5/1932 | Sovatkin |
| 2,186,143 A | 1/1940 | Neugass |
| 2,456,806 A | 12/1948 | Wolffe |
| 2,744,708 A | 5/1956 | Bedford, Jr. |

(Continued)

FOREIGN PATENT DOCUMENTS

| | | | | |
|---|---|---|---|---|
| DE | 201 10 921 | 12/2001 | ............. | A61B 17/42 |
| DE | 695 32 474 | 11/2004 | ............. | A61B 17/42 |

(Continued)

OTHER PUBLICATIONS

Culligan et al., "Long-Term Success of Abdominal Sacral Colpopexy Using Synthetic Mesh," Am. J. Obstet. Gynecol., Dec. 2002.

(Continued)

*Primary Examiner* — Nicholas Plionis
(74) *Attorney, Agent, or Firm* — Fish & Richardson P.C.

(57) ABSTRACT

A uterine manipulator includes an arcuate shaft configured to be inserted into a cervix and a colpotomizer assembly configured to move along the arcuate shaft. The colpotomizer assembly includes a cup configured to receive the cervix. The cup defines a cup face disposed substantially perpendicular to an axial centerline of the cup and having a centerpoint disposed along the axial centerline of the cup, and an opening spaced apart from the cup face and sized to allow passage of the arcuate shaft. The opening is configured such that, when the arcuate shaft is positioned within the opening, an arcuate centerline of the arcuate shaft is aligned with the centerpoint of the cup face, and the arcuate centerline of the arcuate shaft is offset from the axial centerline of the cup at the opening.

23 Claims, 11 Drawing Sheets

(56) References Cited

U.S. PATENT DOCUMENTS

| | | |
|---|---|---|
| 3,096,764 A | 7/1963 | Hiebert |
| 3,131,690 A | 5/1964 | Innis et al. |
| 3,153,267 A | 10/1964 | Rowland, Jr. |
| 3,196,865 A | 7/1965 | Rose |
| 3,749,088 A | 7/1973 | Kohlmann |
| 3,766,909 A | 10/1973 | Ozbey |
| 3,769,983 A | 11/1973 | Merav |
| 3,877,433 A | 4/1975 | Librach |
| 3,878,848 A | 4/1975 | Hiebert |
| 3,948,270 A | 4/1976 | Hasson |
| 4,022,208 A | 5/1977 | Valtchev |
| 4,066,071 A | 1/1978 | Nagel |
| 4,323,057 A | 4/1982 | Jamieson |
| 4,379,457 A | 4/1983 | Gravener et al. |
| 4,430,076 A | 2/1984 | Harris |
| 4,533,349 A | 8/1985 | Bark |
| 4,562,832 A | 1/1986 | Wilder et al. |
| 4,597,030 A | 6/1986 | Brody et al. |
| 4,627,421 A | 12/1986 | Symbas et al. |
| 4,775,362 A | 10/1988 | Kronner |
| 4,807,625 A | 2/1989 | Singleton |
| 4,823,167 A | 4/1989 | Manska et al. |
| 4,981,355 A | 1/1991 | Higgins |
| 4,996,974 A | 3/1991 | Ciarlei |
| 4,997,419 A | 3/1991 | Lakatos et al. |
| 5,037,430 A * | 8/1991 | Hasson ............... A61B 17/42 606/119 |
| 5,059,198 A | 10/1991 | Gimpelson |
| 5,104,377 A | 4/1992 | Levine |
| 5,174,276 A | 12/1992 | Crockard |
| 5,181,842 A | 1/1993 | Sunderland et al. |
| 5,209,754 A | 5/1993 | Ahluwalia |
| 5,232,443 A | 8/1993 | Leach |
| 5,237,985 A | 8/1993 | Hodgson et al. |
| 5,242,240 A | 9/1993 | Gorham |
| 5,259,836 A | 11/1993 | Thurmond et al. |
| 5,273,026 A | 12/1993 | Wilk |
| 5,338,297 A | 8/1994 | Kocur et al. |
| 5,353,784 A | 10/1994 | Nady-Mohamed |
| 5,409,496 A | 4/1995 | Rowden et al. |
| 5,431,662 A | 7/1995 | Nicholas |
| 5,520,698 A | 5/1996 | Koh |
| 5,540,700 A | 7/1996 | Rowden et al. |
| 5,549,563 A | 8/1996 | Kronner |
| 5,571,115 A | 11/1996 | Nicholas |
| 5,624,399 A | 4/1997 | Ackerman |
| 5,643,285 A | 7/1997 | Rowden et al. |
| 5,690,617 A | 11/1997 | Wright |
| 5,810,806 A | 9/1998 | Ritchart et al. |
| 5,835,657 A | 11/1998 | Suarez et al. |
| 5,840,077 A | 11/1998 | Rowden et al. |
| 6,068,121 A | 5/2000 | McGlinch |
| 6,080,118 A | 6/2000 | Blythe |
| 6,159,170 A | 12/2000 | Borodulin et al. |
| 6,328,729 B1 | 12/2001 | Jervis |
| 6,348,036 B1 | 2/2002 | Looney et al. |
| 6,423,075 B1 | 7/2002 | Singh et al. |
| 6,651,992 B1 | 11/2003 | Smith |
| 6,682,100 B2 | 1/2004 | Wood et al. |
| 6,741,895 B1 | 5/2004 | Gafni et al. |
| 6,752,819 B1 | 6/2004 | Brady et al. |
| 6,932,759 B2 | 8/2005 | Kammerer et al. |
| 7,052,453 B2 | 5/2006 | Presthus et al. |
| 7,334,503 B1 | 2/2008 | Newman |
| 8,545,513 B2 | 10/2013 | Blair et al. |
| 8,740,916 B2 | 6/2014 | Blair et al. |
| 8,939,988 B2 | 1/2015 | Auerbach et al. |
| 2001/0021854 A1 | 9/2001 | Donnez et al. |
| 2003/0187334 A1 | 10/2003 | Biswas |
| 2003/0195386 A1 | 10/2003 | Thierfelder et al. |
| 2003/0220538 A1 | 11/2003 | Jacquetin |
| 2004/0122462 A1 * | 6/2004 | Bakos ............... A61B 1/00154 606/191 |
| 2004/0138528 A1 | 7/2004 | Richter et al. |
| 2004/0193043 A1 | 9/2004 | Duchon et al. |
| 2004/0230092 A1 | 11/2004 | Thierfelder et al. |
| 2005/0065395 A1 | 3/2005 | Mellier |
| 2005/0085827 A1 | 4/2005 | G. et al. |
| 2005/0107818 A1 | 5/2005 | Valtchev |
| 2005/0184124 A1 | 8/2005 | Scirica et al. |
| 2005/0277948 A1 | 12/2005 | Cedars et al. |
| 2006/0015001 A1 | 1/2006 | Staskin et al. |
| 2006/0199994 A1 | 9/2006 | Inman et al. |
| 2006/0241652 A1 | 10/2006 | Doll et al. |
| 2007/0088351 A1 | 4/2007 | Ewaschuk et al. |
| 2007/0129615 A1 | 6/2007 | Backman et al. |
| 2007/0135679 A1 | 6/2007 | Hunt et al. |
| 2008/0058833 A1 * | 3/2008 | Rizvi ............... A61B 17/4241 606/119 |
| 2008/0221590 A1 | 9/2008 | Ikeda et al. |
| 2008/0243176 A1 | 10/2008 | Weitzner et al. |
| 2008/0245371 A1 * | 10/2008 | Gruber ............... A61B 1/303 128/831 |
| 2008/0249535 A1 | 10/2008 | Valtchev |
| 2009/0131954 A1 | 5/2009 | Christian et al. |
| 2010/0106163 A1 | 4/2010 | Blair et al. |
| 2010/0152749 A1 | 6/2010 | Von Pechmann et al. |
| 2010/0168784 A1 | 7/2010 | Pustilnik |
| 2010/0179575 A1 | 7/2010 | Von Pechmann et al. |
| 2010/0280309 A1 | 11/2010 | Von Pechmann |
| 2010/0305578 A1 | 12/2010 | Auerbach et al. |
| 2011/0130769 A1 | 6/2011 | Boebel et al. |
| 2012/0109146 A1 | 5/2012 | Auerbach et al. |
| 2012/0109147 A1 | 5/2012 | Auerbach et al. |
| 2012/0323079 A1 | 12/2012 | Bakare et al. |
| 2013/0345714 A1 | 12/2013 | Blair et al. |

FOREIGN PATENT DOCUMENTS

| | | | |
|---|---|---|---|
| DE | 103 41 561 | 4/2005 | ............. A61B 17/00 |
| EP | 0 400 458 | 12/1990 | ............. A61B 1/30 |
| EP | 0 890 342 | 9/2003 | ............. A61B 17/42 |
| WO | WO 2008/074054 | 6/2008 | ............. A61B 1/303 |
| WO | WO 2009/078953 | 6/2009 | ............. A61F 2/00 |

OTHER PUBLICATIONS

"KOH Cup Vaginal Fornices Delineator & Colpo-Pneumo Occluder," *The Koh Colpotomizer™ System*, Directions for Use; 6 pages; Sep. 2008.

"Laparoscopic Hysterectomy and Colpotomy Accessories for Use Exclusively with the RUMI System Uterine Manipulator," *CooperSurgical The KOH Colpotomizer System*; 2 pages; Oct. 2006.

Non-Final Office Action for U.S. Appl. No. 14/510,251 dated Sep. 28, 2016 (21 pages).

* cited by examiner

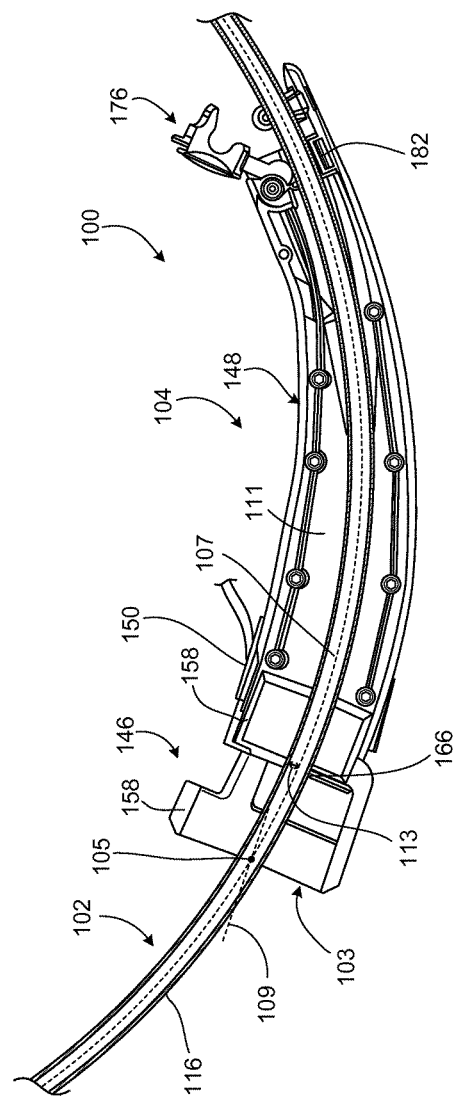

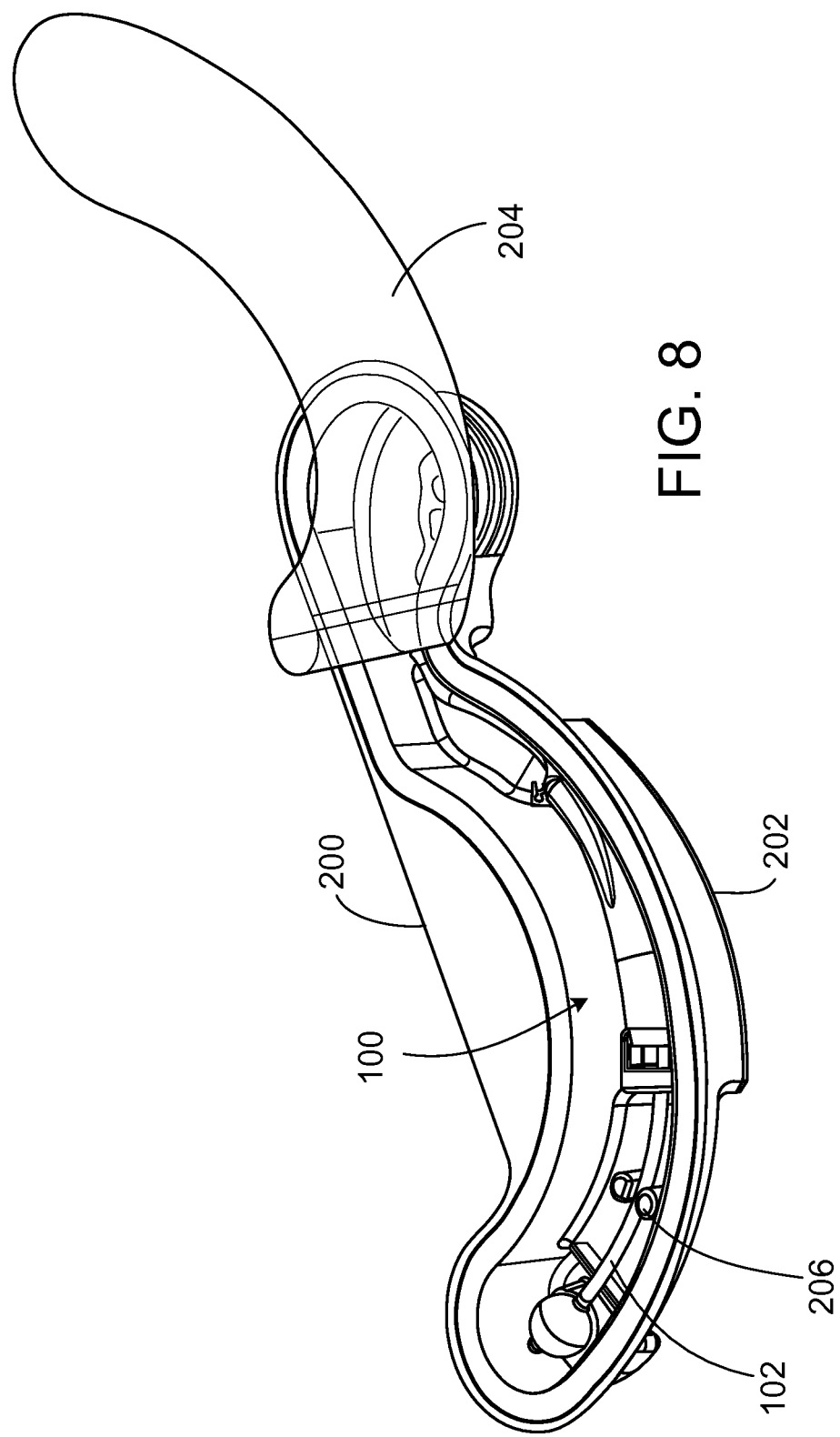

UTERINE MANIPULATORS AND RELATED COMPONENTS AND METHODS

TECHNICAL FIELD

This disclosure relates to uterine manipulators and related components and methods.

BACKGROUND

Uterine manipulators are medical instruments that are used for manipulating (e.g., moving or repositioning) a patient's uterus during medical procedures. Such procedures include surgical procedures, such as laparoscopic gynecologic surgery (e.g., total laparoscopic hysterectomy (TLH) surgery). Instruments of this kind often include a proximal portion that remains external to the patient's body during use and a distal portion that is inserted into the patient's body. The proximal portion typically provides for manipulation of the instrument during use. The distal portion often includes a tip that is sized to be inserted into and/or engage the uterus. Generally, the distal portion of the instrument is advanced through the vaginal cavity and into the uterus. With the distal portion inserted within a uterus, the uterus can be manipulated through surgeon-controlled or physician-controlled movements of the proximal portion. Following completion of a procedure, the instrument is removed from the patient's body via the vaginal cavity.

SUMMARY

In general, this disclosure relates to uterine manipulators and related components and methods. Such uterine manipulators can be used for manipulating a patient's uterus during gynecological surgery and/or gynecological diagnostic procedures.

In one aspect, a uterine manipulator includes an arcuate shaft configured to be inserted into a cervix and a colpotomizer assembly configured to move along the arcuate shaft. The colpotomizer assembly includes a cup configured to receive the cervix. The cup defines a cup face disposed substantially perpendicular to an axial centerline of the cup and having a centerpoint disposed along the axial centerline of the cup, and an opening spaced apart from the cup face and sized to allow passage of the arcuate shaft. The opening is configured such that, when the arcuate shaft is positioned within the opening, an arcuate centerline of the arcuate shaft is aligned with the centerpoint of the cup face, and the arcuate centerline of the arcuate shaft is offset from the axial centerline of the cup at the opening.

In another aspect, a colpotomizer assembly includes a cup configured to receive a cervix. The cup defines a cup face disposed perpendicular to an axial centerline of the cup and having a centerpoint disposed along the axial centerline of the cup and an opening spaced apart from the cup face and sized to allow passage of a shaft. The opening is configured such that, when the shaft is positioned within the opening, an arcuate centerline of the shaft is aligned with the centerpoint of the cup face, and the arcuate centerline of the shaft is offset from the axial centerline of the cup at the opening.

In a further aspect, a method of adjusting a uterine manipulator includes moving a colpotomizer cup of the uterine manipulator along a curved shaft of the uterine manipulator in a manner such that a distal face of the colpotomizer cup remains centered on an arch centerline of the curved shaft and an axial centerline of the colpotomizer cup remains offset from the arch centerline of the curved shaft at an opening of the colpotomizer cup that is spaced proximally from the distal face of the colpotomizer cup.

In a further aspect, a uterine manipulator includes a shaft configured to be inserted into a cervix. The shaft includes multiple ruler markings printed along a portion of the shaft and a colpotomizer assembly configured to move along the shaft. The colpotomizer assembly includes a sleeve that includes a rotatable locking member configured to compress the shaft in a manner that locks the colpotomizer assembly in position along the shaft when the rotatable locking member is depressed against the shaft. The rotatable locking member includes a cam roller configured to compress the shaft when the rotatable locking member is depressed towards the shaft.

In a further aspect, a colpotomizer assembly configured to move along a shaft of a uterine manipulator includes a sleeve that includes a rotatable locking member configured to compress the shaft in a manner that locks the colpotomizer assembly in position along the shaft when the rotatable locking member is depressed against the shaft. The rotatable locking member includes a cam roller configured to compress the shaft when the rotatable locking member is depressed towards the shaft.

In a further aspect, a method of adjusting a uterine manipulator includes moving a colpotomizer sleeve of the uterine manipulator to a predetermined position along a shaft of the uterine manipulator, depressing a rotatable locking member of the colpotomizer sleeve towards the shaft, compressing the shaft with the rotatable locking member of the colpotomizer sleeve to lock the colpotomizer sleeve at the predetermined location, and confirming an accuracy of the position of the colpotomizer sleeve by visualizing a ruler marking printed along the shaft using a magnification lens of the rotatable locking member.

In a further aspect, a uterine manipulator includes a shaft configured to be inserted into a cervix, the shaft defining a central lumen that passes air between a proximal portion of the shaft and a distal tip of the shaft. The uterine manipulator further includes an expandable balloon secured to the distal tip of the shaft and a handle secured to the proximal portion of the shaft. The handle includes an integral syringe that is configured to inflate and deflate the expandable balloon by displacing air within the central lumen of the shaft.

In a further aspect, a method of deploying a uterine manipulator includes inserting a shaft of the uterine manipulator through a cervix, actuating an integral syringe within a handle that is secured to a proximal portion of the shaft, and inflating an expandable balloon that is secured to a distal tip of the uterine manipulator.

Implementations may provide one or more of the following features.

In some embodiments, the arcuate shaft includes a proximal portion, a central portion along which the colpotomizer assembly can move, and a distal tip.

In certain embodiments, the arcuate shaft is a rigid shaft.

In some embodiments, the cup includes a cup body that defines the cup face at a distal end of the cup.

In certain embodiments, the cup body is configured to receive the cervix.

In some embodiments, the cup body defines multiple viewing windows for visualizing the cervix within the cup body.

In certain embodiments, the cup body defines a beveled rim configured to provide an anatomical landmark and an incision backstop.

In some embodiments, the cup includes a base defining the opening.

In certain embodiments, when the arcuate shaft is disposed within the opening, the arcuate centerline of the arcuate shaft is offset by about 0.065 inch to about 0.085 inch from the axial centerline of the cup at the opening.

In some embodiments, the colpotomizer assembly further includes a sleeve connected to the cup and defining a channel configured to receive the arcuate shaft.

In certain embodiments, the sleeve includes a locking member configured to lock the colpotomizer assembly at any of multiple different locations along the arcuate shaft.

In some embodiments, the colpotomizer assembly further includes a vaginal occluder.

In certain embodiments, the uterine manipulator further includes a manipulator handle secured to the arcuate shaft.

In some embodiments, the manipulator handle includes an integrated syringe configured to displace air within a central lumen of the arcuate shaft.

In certain embodiments, the uterine manipulator further includes an expandable balloon disposed along a distal tip of the arcuate shaft and in fluid communication with the central lumen of the arcuate shaft.

In some embodiments, the integrated syringe is configured to deliver air to and withdraw air from the expandable balloon.

In certain embodiments, the uterine manipulator further includes an integrated light source mounted to a distal tip of the arcuate shaft.

In some embodiments, the manipulator handle includes a power source for powering the integrated light source.

In certain embodiments, the uterine manipulator is a single-use device.

In some embodiments, the uterine manipulator further includes a shrink tube disposed about the arcuate shaft for facilitating movement of the colpotomizer assembly along the arcuate shaft and locking of the colpotomizer assembly along the shaft.

In certain embodiments, the cup body defines a recess configured to receive a cervix.

In some embodiments, the opening is configured to receive an arcuate shaft.

In certain embodiments, the sleeve includes a locking member configured to lock the colpotomizer assembly at a predetermined location along the shaft.

In some embodiments, the colpotomizer cup includes a body that defines the distal face.

In certain embodiments, the body defines multiple viewing windows for visualizing the cervix within the body.

In some embodiments, at the opening of the colpotomizer cup, the axial centerline of the colpotomizer cup remains offset from the arcuate centerline of the curved shaft by about 0.065 inch to about 0.085 inch.

In certain embodiments, moving the colpotomizer cup includes moving a sleeve that is connected to the colpotomizer cup.

In some embodiments, the sleeve defines a channel configured to receive the curved shaft.

In certain embodiments, the method further includes locking the colpotomizer sleeve at a predetermined location along the curved shaft.

In some embodiments, the shaft is a rigid shaft.

In certain embodiments, the uterine manipulator further includes a shrink tube that surrounds a portion of the shaft, such that when the rotatable locking member is depressed towards the shaft, the rotatable locking member compresses the shrink tube.

In some embodiments, the shrink tube has a hardness of about shore D25 to about shore D60.

In certain embodiments, the sleeve defines a channel configured to receive the shaft.

In some embodiments, the rotatable locking member includes a lens configured to magnify a ruler marking of the multiple ruler markings when the rotatable locking member is depressed against the shaft.

In certain embodiments, the rotatable locking member includes a roller mount that extends from the cam roller, and the sleeve defines a receptacle configured to receive the roller mount of the rotatable locking member.

In some embodiments, the sleeve includes opposing projections, and the rotatable locking member includes a jaw configured snap fit onto the opposing projections for securing the rotatable locking member in a locked configuration.

In certain embodiments, the rotatable locking member includes a lift flange for rotating the rotatable locking member away from the shaft and into an open configuration.

In some embodiments, the multiple ruler markings indicate a distance between a base of a cup of the colpotomizer assembly and a distal end of the shaft.

In some embodiments, the colpotomizer assembly further includes a cup configured to receive the cervix and that is attached to the sleeve.

In certain embodiments, the cup is configured such that a distal face of the cup remains centered on an arch centerline of the shaft as the colpotomizer assembly is moved along the shaft and such that an axial centerline of the cup remains offset from the arch centerline of the shaft at an opening of the cup that is spaced proximally from the distal face of the cup.

In certain embodiments, the uterine manipulator further includes a manipulator handle.

In some embodiments, the manipulator handle includes an integrated syringe configured to displace air within a central lumen of the shaft.

In certain embodiments, the uterine manipulator further includes an expandable balloon disposed along a distal tip of the shaft and in fluid communication with the central lumen of the shaft.

In some embodiments, the sleeve defines a channel that surrounds the shaft.

In certain embodiments, the rotatable locking member includes a lens configured to magnify a ruler marking printed along the shaft when the rotatable locking member is depressed against the shaft.

In some embodiments, the ruler marking indicates a distance between a base of a cup of the colpotomizer assembly and a distal end of the shaft.

In certain embodiments, the rotatable locking member includes a roller mount that extends from the cam roller, and the sleeve defines a receptacle configured to receive the roller mount of the rotatable locking member.

In some embodiments, the cup is configured such that a distal face of the cup remains centered on an arch centerline of the shaft as the colpotomizer assembly is moved along the shaft and such that an axial centerline of the cup remains offset from the arch centerline of the shaft at an opening of the cup that is spaced proximally from the distal face of the cup as the cup is moved along the shaft.

In certain embodiments, the colpotomizer sleeve defines a channel configured to receive the shaft.

In some embodiments, compressing the shaft with the rotatable locking member includes rotating a cam roller of the rotatable locking member into a shrink tube surrounding the shaft.

In certain embodiments, depressing the rotatable locking member towards the shaft includes rotating a roller mount of the rotatable locking member within receptacles of the colpotomizer sleeve.

In some embodiments, compressing the shaft with the rotatable locking member includes snap fitting a jaw of the rotatable locking member onto opposing projections of the colpotomizer sleeve for securing the rotatable locking member in a locked configuration.

In certain embodiments, the method further includes moving a lift flange of the rotatable locking upwards for rotating the rotatable locking member away from the shaft and into an open configuration.

In some embodiments, the ruler marking indicates a distance between a base of a colpotomizer cup secured to the colpotomizer sleeve and a distal end of the shaft.

In certain embodiments, moving the colpotomizer sleeve along the shaft includes moving a colpotomizer cup configured to receive a cervix and that is attached to the colpotomizer sleeve.

In some embodiments, the colpotomizer cup is configured such that a distal face of the colpotomizer cup remains centered on an arch centerline of the shaft as the colpotomizer cup is moved along the shaft and such that an axial centerline of the cup remains offset from the arch centerline of the shaft at an opening of the cup that is spaced proximally from the distal face of the cup as the colpotomizer cup is moved along the shaft.

In certain embodiments, the moving, the depressing, and the compressing is performed in a one-handed process.

In some embodiments, the integral syringe includes a body and a plunger configured to move within the body to displace air.

In certain embodiments, a proximal portion of the shaft extends into the body of the plunger.

In some embodiments, the plunger includes a button that is slidable along the handle.

In certain embodiments, the expandable balloon is inflated when the button is moved distally, and the expandable balloon is deflated when the button is moved proximally.

In some embodiments, the integral syringe includes one or more detents that maintain the button in a proximal or a distal position.

In certain embodiments, the shaft defines an opening that passes air between the central lumen of the shaft and the expandable balloon.

In some embodiments, the handle defines multiple depressions that together provide a grip for grasping the handle.

In certain embodiments, the uterine manipulator further includes an integrated light source mounted to the distal tip of the shaft.

In some embodiments, the power source includes one or more electrical wires that extend within the central lumen of the shaft from the power source to the integrated light source.

In certain embodiments, the integrated light source is an LED.

In some embodiments, the uterine manipulator further includes a colpotomizer assembly that is movable along the shaft.

In certain embodiments, the colpotomizer assembly includes a cup that is configured to receive a cervix.

In some embodiments, the cup is configured such that a distal face of the cup remains centered on an arch centerline of the shaft as the cup is moved along the shaft and such that an axial centerline of the cup remains offset from the arch centerline of the shaft at an opening of the cup that is spaced proximally from the distal face of the cup as the colpotomizer assembly is moved along the shaft.

In certain embodiments, the colpotomizer assembly includes a sleeve that is configured to lock the colpotomizer assembly in position along the shaft.

In some embodiments, the shaft is a rigid cannula.

In certain embodiments, the shaft is a curved shaft.

In some embodiments, the method further includes determining a depth of a uterus at which to insert the shaft through the cervix.

In certain embodiments, the shaft defines a central lumen that passes air between the integral syringe and the expandable balloon.

In some embodiments, actuating the integral syringe includes moving a plunger of the integral syringe distally along the handle to deliver air to the expandable balloon.

In certain embodiments, the method includes moving a plunger of the integral syringe proximally along the handle to withdraw air from the expandable balloon, and deflating the expandable balloon.

In some embodiments, the shaft defines an opening that passes air between the central lumen of the shaft and the expandable balloon.

In certain embodiments, the method further includes grasping the handle along multiple depressions defined by the handle.

In some embodiments, the method further includes powering a light source mounted to the distal tip of the shaft.

In some embodiments, the method further includes moving a colpotomizer assembly of the uterine manipulator into an operational position.

In some embodiments, the method further includes locking the colpotomizer assembly along the shaft at the operational position.

Implementations may provide one or more of the following advantages.

In some embodiments, a geometry (e.g., provided by the position and size of an opening within a colpotomizer cup base) ensures proper alignment of a cup face with respect to a shaft of the uterine manipulator. In particular, a centerpoint of the cup face is maintained along an arch centerline of the shaft. Such a configuration is imposed by an offset between a centerline of the colpotomizer cup (along which the centerpoint of the cup face lies) and the arch centerline of the shaft, at the position of the opening in the colpotomizer cup base. Such alignment of the colpotomizer cup with respect to the shaft ensures that an appropriately angled cutting edge is achieved for guiding a cutting of the uterus with an even distribution of tissue when the cervix is received within the colpotomizer cup. This geometry prevents positioning of the uterine manipulator with a mis-oriented cutting edge, which could lead to undesirable effects following the procedure.

In certain embodiments, the uterine manipulator includes a one-handed locking mechanism that allows a colpotomizer assembly to be locked into a desired position along a shaft of the uterine manipulator. The locking mechanism can include a thumb lock that can be actuated with the same hand that moves the colpotomizer assembly along the shaft. The thumb lock provides the user with the ability to easily position and lock the colpotomizer assembly at any of various different positions along the shaft of the uterine manipulator. The thumb lock includes a cam roller that has a variable radius, such that the cam roller can compress (e.g., dig into) a shrink tube as the cam roller is rotated towards the shaft of the uterine manipulator, thereby providing resistance to movement of the colpotomizer assembly along the shaft. The mechanical integrity of the thumb lock may be maintained over multiple (e.g., four) lock-unlock cycles.

In some embodiments, a convex lens of the thumb lock magnifies ruler markings printed along the shaft, such that a ruler marking substantially fills a viewing window of the lens. Such magnification assists the user of the uterine manipulator in visualizing the ruler markings to determine an appropriate position of the colpotomizer assembly along the shaft. Proper placement of the uterine manipulator with respect to a fundus of the uterus, as aided by the lens of the thumb lock and the ruler markings along the shaft, can prevent perforation and other damage to the fundus and the distal region of the uterus. Furthermore, the alignment of the lens with the ruler marking and the ability to view placement of the cervix within the colpotomizer cup through viewing windows helps to ensure that the colpotomizer cup is fully forward in the desired position relative to a distal tip of the shaft and relative to the cervix.

In certain embodiments, a manipulator handle includes an integral syringe for injecting air into and removing air from a central lumen of a shaft of the uterine manipulator to inflate and deflate an expandable balloon in fluid communication with the central lumen. Button actuation of the syringe can provide the user with a simple, ergonomic, and one-handed mechanism for inflating and deflating the expandable balloon during a surgical procedure. Furthermore, finger depressions positioned along the manipulator handle provide an ergonomic grip for grasping and positioning the uterine manipulator.

In some embodiments, an integral light source mounted to a distal tip of a shaft of the uterine manipulator can be used to illuminate the vaginal cavity and external orifice of the uterus (cervical os) during insertion of the uterine manipulator. The light source and the distal tip provide an atraumatic surface that allows the uterine manipulator to be inserted in the patient without damaging tissues of the vaginal cavity, cervix, or uterus. The light source can be turned on and off by actuating a button disposed along a distal region of a manipulator handle and optimally positioned for a right-handed or left-handed use. Button actuation of integral light source can provide the user with a simple, ergonomic, and one-handed mechanism for increasing visibility during insertion of the uterine manipulator.

In some embodiments, materials (e.g., 304 SS or 304 SS full hard) from which a shaft of the manipulator is constructed can advantageously provide tactile feedback to the user as the shaft is inserted or positioned within the patient. Certain portions of the shaft are covered by a shrink tube that provides lubricity for sliding of a colpotomizer assembly along the shaft and traction for locking the colpotomizer assembly in a desired position. The shrink tube can have a certain hardness that provides the shrink tube with enough traction to securely lock the colpotomizer assembly in the desired position.

In certain embodiments, the ability to displace a colpotomizer assembly can allow for quicker and easier positioning of a distal tip of a shaft of the uterine manipulator within the cervix since a procedure can be performed without visual obstruction of the colpotomizer assembly.

In certain embodiments, the uterine manipulator can be provided as a disposable (e.g., single-use) surgical device.

Other aspects, features, and advantages will be apparent from the description, the drawings, and the claims.

DESCRIPTION OF DRAWINGS

FIG. 6 is a cross-sectional side view of a portion of the uterine manipulator of FIG. 1.

FIG. 8 is a perspective view of the uterine manipulator of FIG. 1 provided in a packaging container.

DETAILED DESCRIPTION

Figure 1:
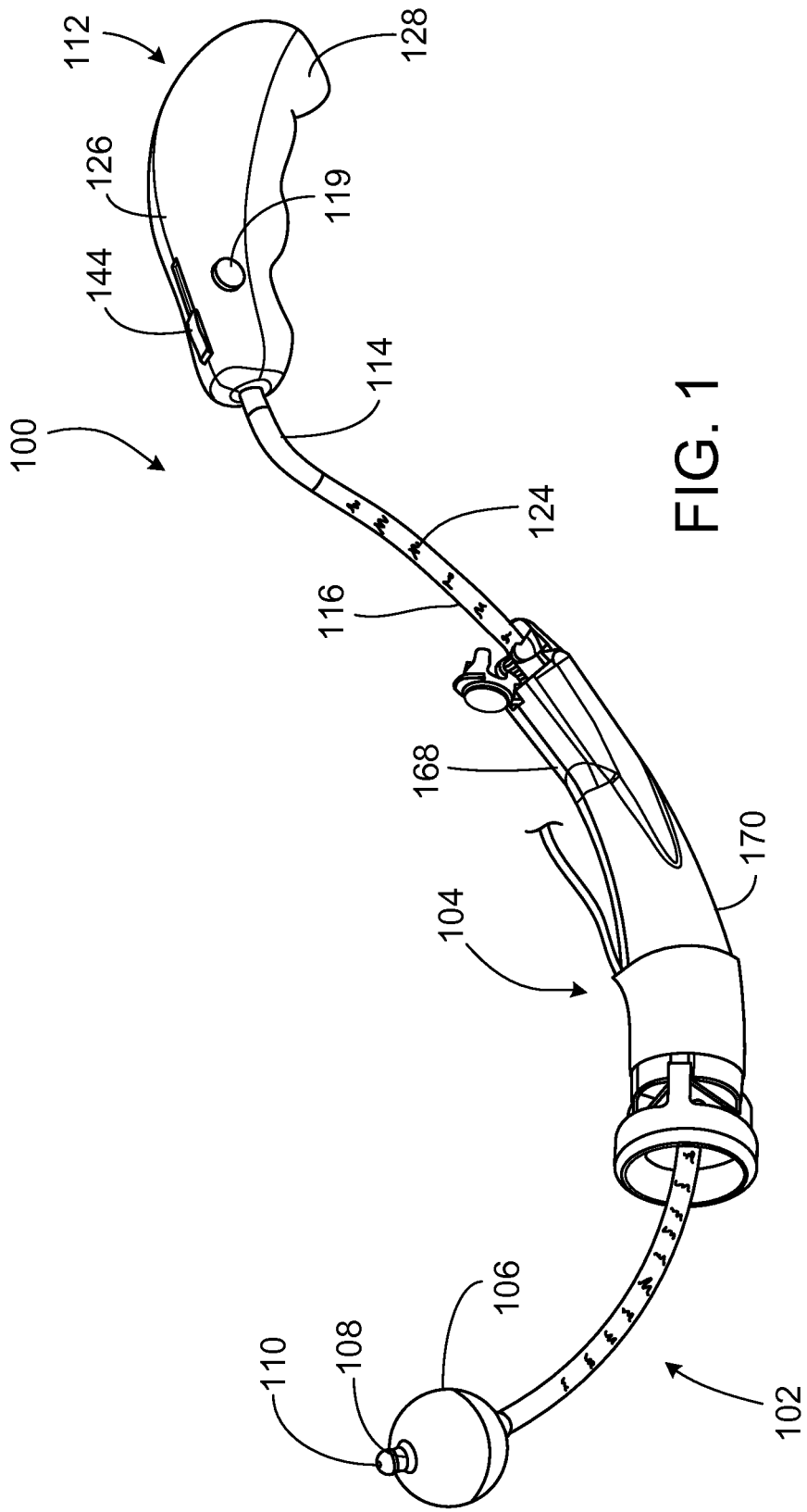
FIG. 1 is a perspective view of a uterine manipulator including a manipulator handle, a shaft, an expandable balloon, a light source, and a colpotomizer assembly.

FIG. 1 illustrates a uterine manipulator 100 adapted for insertion into a vaginal cavity for use in female pelvic surgical procedures. The uterine manipulator 100 includes a shaft 102 configured to extend within a cervix for use in repositioning a uterus and a colpotomizer assembly 104 disposed about the shaft 102 and configured to receive the cervix. The uterine manipulator 100 further includes an expandable balloon 106 secured to a distal tip 108 of the shaft 102 and configured to maintain a position of the distal tip 108 within the uterus. A light source 110 is mounted to the distal tip 108 of the shaft 102 and can be used to illuminate the vaginal cavity and external orifice of the uterus (i.e., the cervical os) during insertion of the uterine manipulator 100. A manipulator handle 112 is connected to a proximal portion 114 of the shaft 102.

Figure 2:
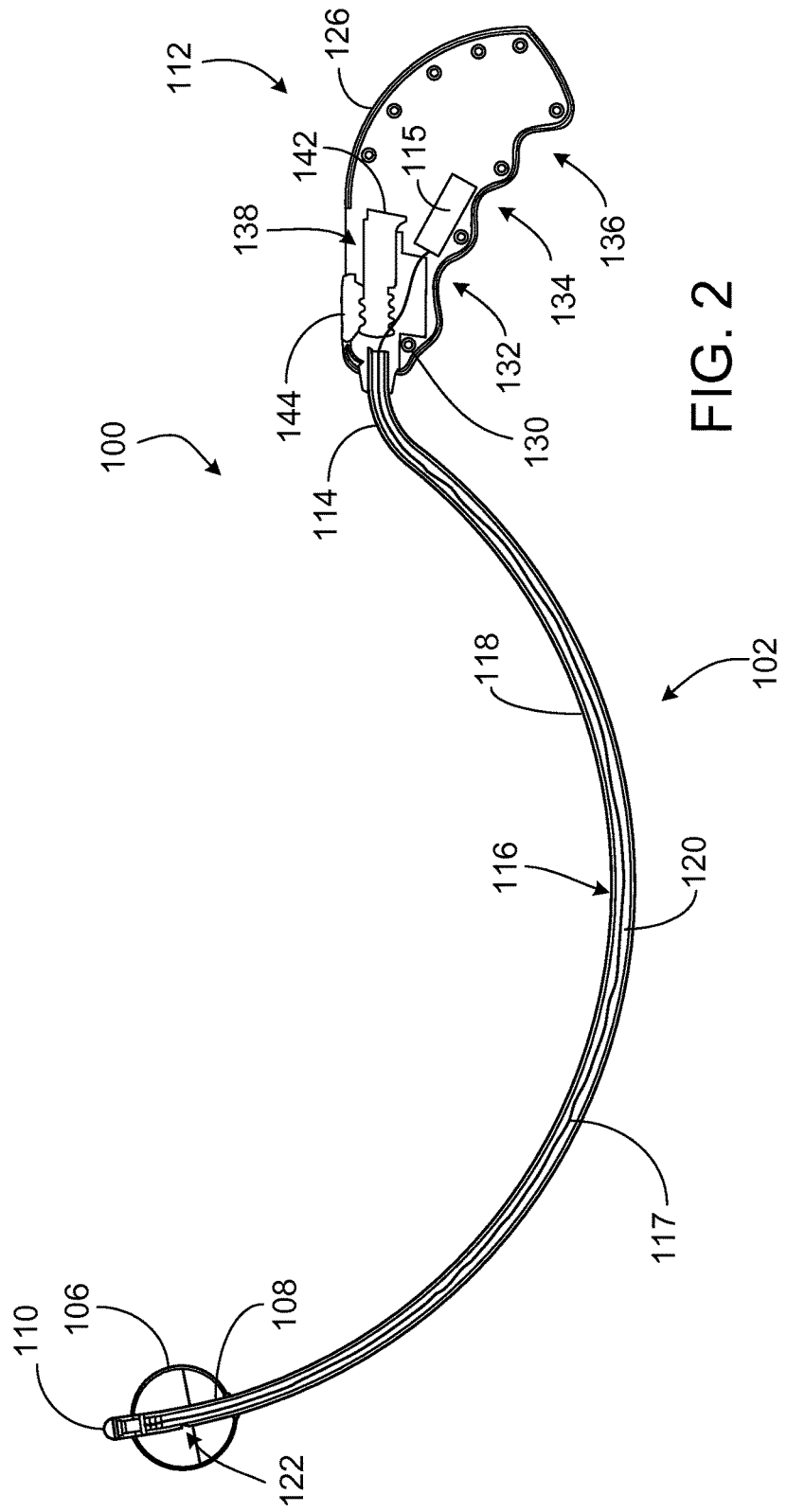
FIG. 2 is a cross-sectional side view of the uterine manipulator of FIG. 1, shown without the colpotomizer assembly.

Referring to FIG. 2, the shaft 102 of the uterine manipulator 100 is formed as a rigid cannula that has a generally curved (e.g., arcuate) shape. The shaft 102 includes the proximal portion 114 that extends into the manipulator handle 112, a central portion 116 along which the colpotomizer assembly 104 is displaceable for engaging the cervix, and the distal tip 108 configured to extend through the cervix and into the uterus. The central portion 116 and a section of the proximal portion 114 that extends distally from the manipulator handle 112 are covered by a shrink tube 118 that provides lubricity for sliding of the colpotomizer assembly 104 along the shaft 102 and traction for locking the colpotomizer assembly 104 in a desired position along the shaft 102, as will be discussed in more detail with respect to FIG.

4. The shrink tube 118 typically has a thickness of about 0.010 inch to about 0.020 inch (e.g., about 0.014 inch to about 0.018 inch).

The shaft 102 of the uterine manipulator 100 defines a central lumen 120 that allows passage of air between the manipulator handle 112 and the expandable balloon 106. The central lumen 120 of the shaft 102 also allows passage of one or more electrical wires 117 from a power source 115 (e.g., a battery) disposed within the manipulator handle 112 to the light source 110 secured to the distal tip 108 of the shaft 102. The shaft 102 also defines an opening 122 located along the distal tip 108 that allows passage of air between the central lumen 120 and the expandable balloon 106 for inflating and deflating the expandable balloon 106. The shaft 102 further includes a set of ruler markings 124 (shown in FIGS. 1 and 3) printed across the shrink tube 118 along the central portion 116 and that indicate a distance from the fundus of the uterus when the uterine manipulator 100 is appropriately, fully inserted into the uterus (e.g., when the distal tip 108 of the shaft 102 is positioned adjacent the fundus, as will be discussed in more detail with respect to FIG. 8). The ruler markings 124 may be provided in English units (e.g., inches) or S.I. units (e.g., mm or cm).

The shaft 102 (e.g., including the section of the proximal portion 114 extending from the manipulator handle 112, the central portion 116, and the distal tip 108) typically has a length of about 11.0 inches to about 12.0 inches (e.g., about 11.4 inches to about 11.7 inches. The section of the proximal portion 114 extending from the manipulator handle 112 typically has a radius of curvature of about 5.0 inches to about 7.0 inches (e.g., about 6.0 inches). The central portion 116 of the shaft 102 typically has a radius of curvature of about 5.50 inches to about 7.00 inches (e.g., about 6.00 inches to about 6.25 inches). The distal tip 108 of the shaft 102 typically has a length of about 0.50 inch to about 0.60 inch (e.g., about 0.55 inch to about 0.56 inch). The shaft 102 typically has an inner diameter of about 0.100 inch to about 0.150 inch (e.g., about 0.128 inch to about 0.134 inch) and a wall thickness of about 0.020 inch to about 0.040 inch (e.g., about 0.027 inch to about 0.029 inch).

The expandable balloon 106 is secured at opposite ends to the distal tip 108 of the shaft 102. The balloon 106 can be secured to the shaft 102 via chemical bonding and compressive capture via the shrink tube. The expandable balloon 106 surrounds the opening 122 along the distal tip 108 and accordingly is in fluid communication with the central lumen 120 of the shaft 102. The expandable balloon 106 can be rapidly inflated and rapidly deflated by syringe actuation that occurs at the manipulator handle 112. The expandable balloon 106 typically has a length of about 1.2 inches to about 1.8 inches (e.g., about 1.4 inches to about 1.6 inches). In a fully inflated state, the expandable balloon 106 typically has a maximum diameter of about 0.60 inch to about 0.80 inch (e.g., about 0.66 inch to about 0.68 inch).

Still referring to FIG. 2, the light source 110 can be secured to the distal tip 108 of the shaft 102 via crimping or chemical bonding and is typically provided as a light-emitting diode (LED). The light source 110, together with the distal tip 108, forms an atraumatic surface that allows the uterine manipulator 100 to be inserted in the patient without damaging tissues of the vaginal cavity, cervix, or uterus. The light source 110 can be turned on and off by actuating a button 119 (e.g., a push button or a slidable button) that is disposed along the manipulator handle 112 and that is electrically coupled to the power source disposed within the manipulator handle 112. The button may generally be disposed along a distal region of the manipulator handle 112 and may be optimally positioned for a right-handed or left-handed user (e.g., a surgeon) of the uterine manipulator 100. Button actuation of the integral light source 110 can provide the user of the uterine manipulator 100 with a simple, ergonomic, and one-handed mechanism for increasing visibility during insertion of the uterine manipulator. The light source 110 can receive power via the one or more electrical wires that extend within the central lumen 120 between the power source and the light source 110. The light source 110 typically operates (e.g., emits light) at a power dissipation of about 100 mW to about 140 mW (e.g., about 108 mW to about 132 mW).

Referring now to FIGS. 1 and 2, the manipulator handle 112 is formed as a clam shell structure that includes a female portion 126 and a male portion 128. The female and male portions 126, 128, respectively, include multiple receptacles 130 (e.g., hexagonal shaped receptacles) and multiple pins (e.g., round or cylindrical shaped pins) positioned along peripheral edges and aligned to mate with each other to hold the female and male portions 126, 128 together. The manipulator handle 112 includes finger depressions 132, 134, 136 that provide a grip to allow the user of the uterine manipulator 100 to ergonomically grip the manipulator handle 112. The manipulator handle 112 further includes an integral syringe 138 for injecting air into and removing air from the central lumen 120 of the shaft 102 to inflate and deflate the expandable balloon 106 in fluid communication with the central lumen 120. A body 140 of the syringe 138 extends distally from the manipulator handle 112 and surrounds an end of the proximal portion 114 of the shaft 102, such that the shaft 102, surrounded by the shrink tube 118 along its proximal portion 114, terminates within the body 140 of the syringe 138. The syringe 138 further includes a plunger 142 that can be actuated (e.g., slid proximally and distally) via a slidable button 144 to inject air into and remove air from the central lumen 120 of the shaft 102. The syringe 138 further includes one or more internal detents in contact with a bottom surface of the button 144 that serve to secure the button 144 in a proximal or distal position upon the button 144 being slid past the detents. Button actuation of the integral syringe 138 can provide the user of the uterine manipulator 100 with a simple, ergonomic, and one-handed mechanism for inflating and deflating the expandable balloon 106 during a surgical procedure.

The shaft 102, the expandable balloon 106, the manipulator handle 112, and the shrink tube 118 of the uterine manipulator 100 can be formed (e.g., molded and/or machined) from one or more materials that are biocompatible and capable of withstanding medical device sterilization procedures, such as chemical-based methods or heat-based methods. In some embodiments, the shaft 102 (e.g., including the proximal portion 114, the central portion 116, and the distal tip 108) can be made of 304 SS and/or 304 SS full hard. Such materials can advantageously provide tactile feedback (e.g., resistance to movement of tissue) to the user of the uterine manipulator 100 as the shaft 102 is inserted or positioned within the patient. In some embodiments, the expandable balloon 106 can be made of silicone, polyvinyl chloride (PVC) or a thermal plastics rubber elastomer (TPRE). In some embodiments, the manipulator handle 112 can be made of polycarbonate or Acrylonitrile butadiene styrene (ABS). In some embodiments, the shrink tube 118 can be made of acrylated olefin and can have a shore durometer of about shore D25 to about shore D60. Such a hardness can provide the shrink tube 118 with enough traction to lock the colpotomizer assembly 104 in a desired location, as will be discussed in more detail with respect to FIGS. 3 and 4. While certain examples of materials from which the shaft 102, the expandable balloon 106, the manipulator handle 112, and the shrink tube 118 can be formed have been provided, it should be understood that a variety of other materials can alternately be used to form these components.

Figure 3:
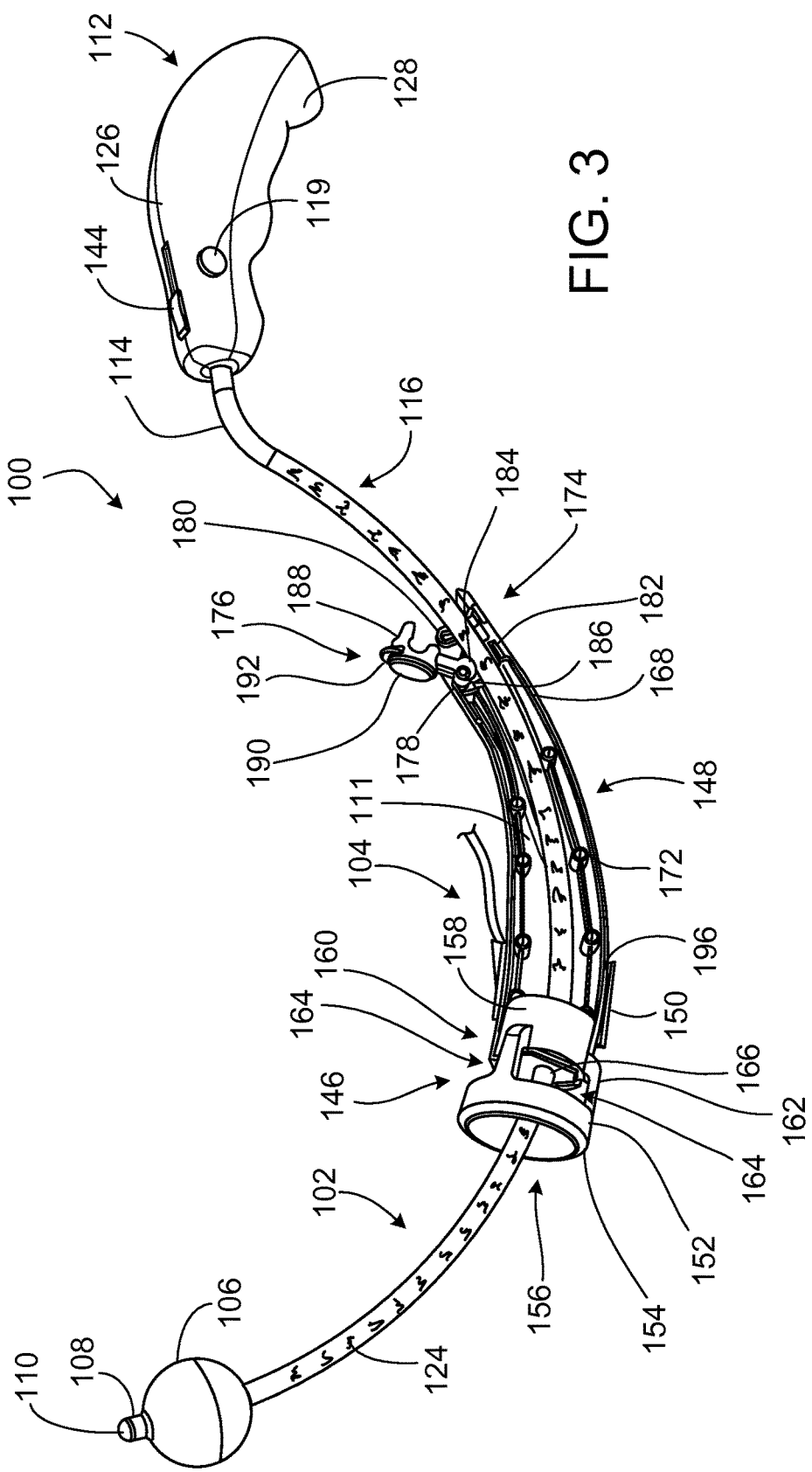
FIG. 3 is a perspective view of a portion of the uterine manipulator of FIG. 1, shown with portions of the colpotomizer assembly removed and with the colpotomizer assembly in an unlocked configuration.

Referring to FIGS. 1 and 3, the colpotomizer assembly 104 is a displaceable assembly that may be slid along the shaft 102 of the uterine manipulator 100. The ability to displace the colpotomizer assembly 104 can allow for quicker and easier positioning of the distal tip 108 of the shaft 102 within the cervix since this procedure can be performed without the visual obstruction of the colpotomizer assembly 104. Then, once proper placement of the distal tip 108 is visually confirmed, the colpotomizer assembly 104 can be advanced along the shaft 102 into engagement with the cervix. The colpotomizer assembly 104 includes a colpotomizer cup 146 adapted to receive the cervix, a sleeve 148 that is connected to the colpotomizer cup 146 and that can be grasped for moving the colpotomizer assembly 104, and a vaginal occluder 150 disposed about a distal cuff 196 of the sleeve 148.

Referring particularly to FIG. 3, the colpotomizer cup 146 includes an annular body 152, a rim 154 located at a distal end 156 of the body 152, and a base 158 located at a proximal end 160 of the body 152. The rim 154 is beveled to permit anatomical landmark and incision backstop during use of the uterine manipulator 100. The body 152 includes three projections 162 that extend to the base 158 and define three viewing windows 164. The base 158 of the colpotomizer cup 146 defines an opening 166 sized to allow passage of the shaft 102. As shown in FIG. 6, a wall of the opening 166 defines a cylindrical profile through which the shaft 102 passes. Referring again to FIG. 3, the sleeve 148 extends proximally from the base 158 of the colpotomizer cup 146 and has an arcuate shape that generally follows the shape of the central portion 116 of the shaft 102. The sleeve 148 is formed as a clam shell structure that includes a female portion 168 and a male portion 170 (shown in FIG. 1). The female and male portions 168, 170, respectively, include multiple receptacles 172 (e.g., hexagonal shaped receptacles) and multiple pins (e.g., round or cylindrical shaped pins) positioned along peripheral edges and aligned to mate with each other to secure the female and male portions 168, 170 together. The female and male portions 168, 170 together define a channel 111 through which the shaft 102 extends.

At a proximal end 174 of the sleeve 148, the sleeve 148 includes a thumb lock 176, opposing receptacles 178 that receive the thumb lock 176, opposing projections 180 to which the thumb lock 176 can be snap fitted, and a guide surface 182 that appropriately guides the sleeve 148 along the shaft 102 and supports the shaft 102 for contact with the thumb lock 176. The thumb lock 176, receptacles 178, projections 180, and guide surface 182 together provide a quick, one-handed locking mechanism that allows the colpotomizer assembly 104 to be locked into a desired position along the shaft 102.

Figure 4:
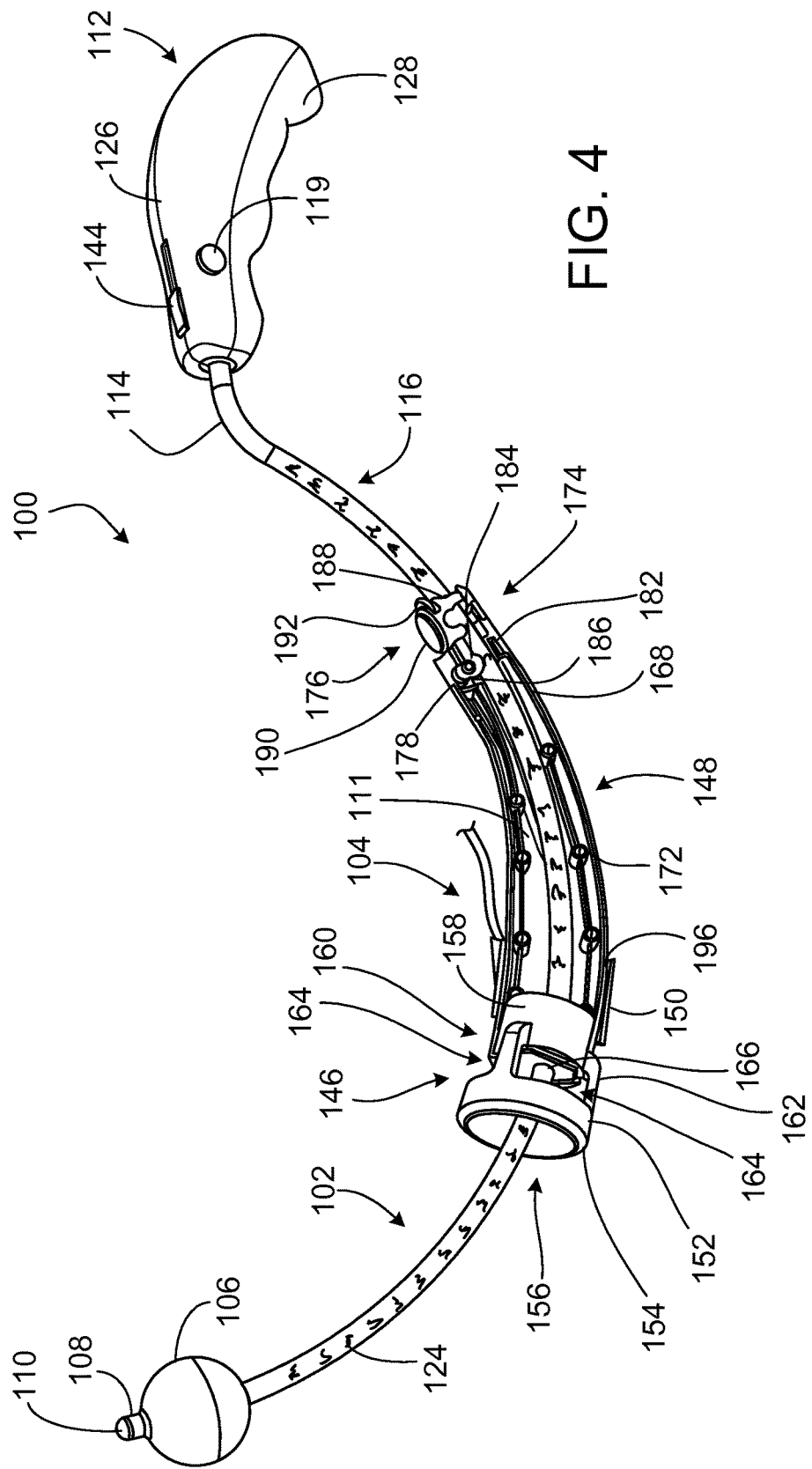
FIG. 4 is a perspective view of a portion of the uterine manipulator of FIG. 1, shown with portions of the colpotomizer assembly removed and with the colpotomizer assembly in a locked configuration.

Referring to FIGS. 3 and 4, the thumb lock 176 includes a cam roller 184 adapted to contact the shrink tube 118 surrounding the shaft 102 to lock the colpotomizer assembly 104 into a selected position along the shaft 102. In particular, the radius of the cam roller 184 is variable (e.g., extending radially beyond a minimum circumference of the cam roller 184 along certain portions of the cam roller 184), such that the cam roller 184 compresses (e.g., digs into) the shrink tube 188 as the cam roller 184 is rotated towards the shaft 102 of the uterine manipulator 100. The thumb lock 176 further includes a roller mount 186 adjacent the cam roller 184, a jaw 188 extending from the cam roller 184, a lens 190 disposed atop the jaw 188, and a lift flange 192 extending proximally from the jaw 188. The lens 190 is a convex lens that magnifies the ruler markings 124 printed along the shaft 102. The focal point of the lens 190 is selected such that a ruler marking 124 substantially fills the viewing window of the lens 190. Such magnification assists the user of the uterine manipulator 100 in visualizing the ruler markings 124 to determine the position of the colpotomizer assembly 104 along the shaft 102. The roller mount 186 is adapted to extend into and rotate within the receptacles 178.

The thumb lock 176 allows the colpotomizer assembly 104 to be locked into a desired position using an easy, one-handed technique that can be carried out with the same hand that moves the colpotomizer assembly 104 along the shaft 102. When the lens 190 or the lift flange 192 is pushed downward (e.g., by the user's thumb) towards the shaft 102 to place the thumb lock 176 in a closed configuration (shown in FIG. 4), rotation of the roller mount 186 and associated rotation of the cam roller 184 causes the cam roller 184 to dig into the shrink tube 118, thereby generating friction that locks the sleeve 148 of the colpotomizer assembly 104 in position along the shaft 102. The cam roller 184 of the thumb lock 176 is configured to apply a compressive load of up to about 5 lb to about 10 lb (e.g., about 7 lb to about 8 lb) on the shaft 102. Such downward force applied to the lens 190 or to the lift flange 192 also causes the jaw 188 to snap fit onto the projections 180. When the lift flange 192 is pushed upward (e.g., by the user's thumb) away from the shaft 102 to place the thumb lock 176 in an open configuration (shown in FIG. 3), rotation of the roller mount 186 and associated rotation of the cam roller 184 causes the cam roller 184 to release the shrink tube 118, thereby unlocking the sleeve 148 of the colpotomizer assembly 104 with respect to the shaft 102. Such upward force applied to the lift flange 192 also causes the jaw 188 to separate from the projections 180. The thumb lock 176 provides the user with the ability to lock the colpotomizer assembly 104 at various different positions along the shaft 102 of the uterine manipulator 100.

Figure 5:
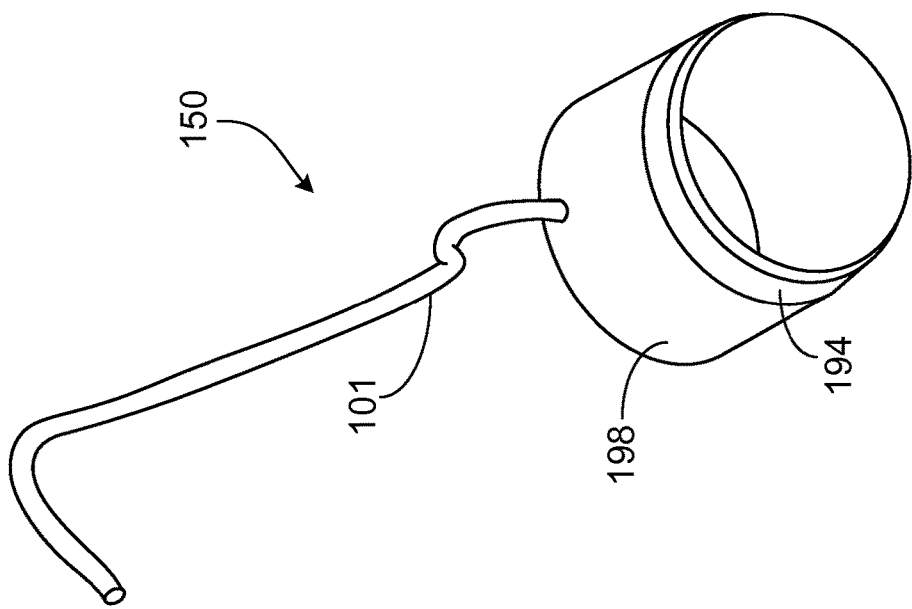
FIG. 5 is a perspective view of a vaginal occluder of the colpotomizer assembly of FIG. 1.
Figure 9:
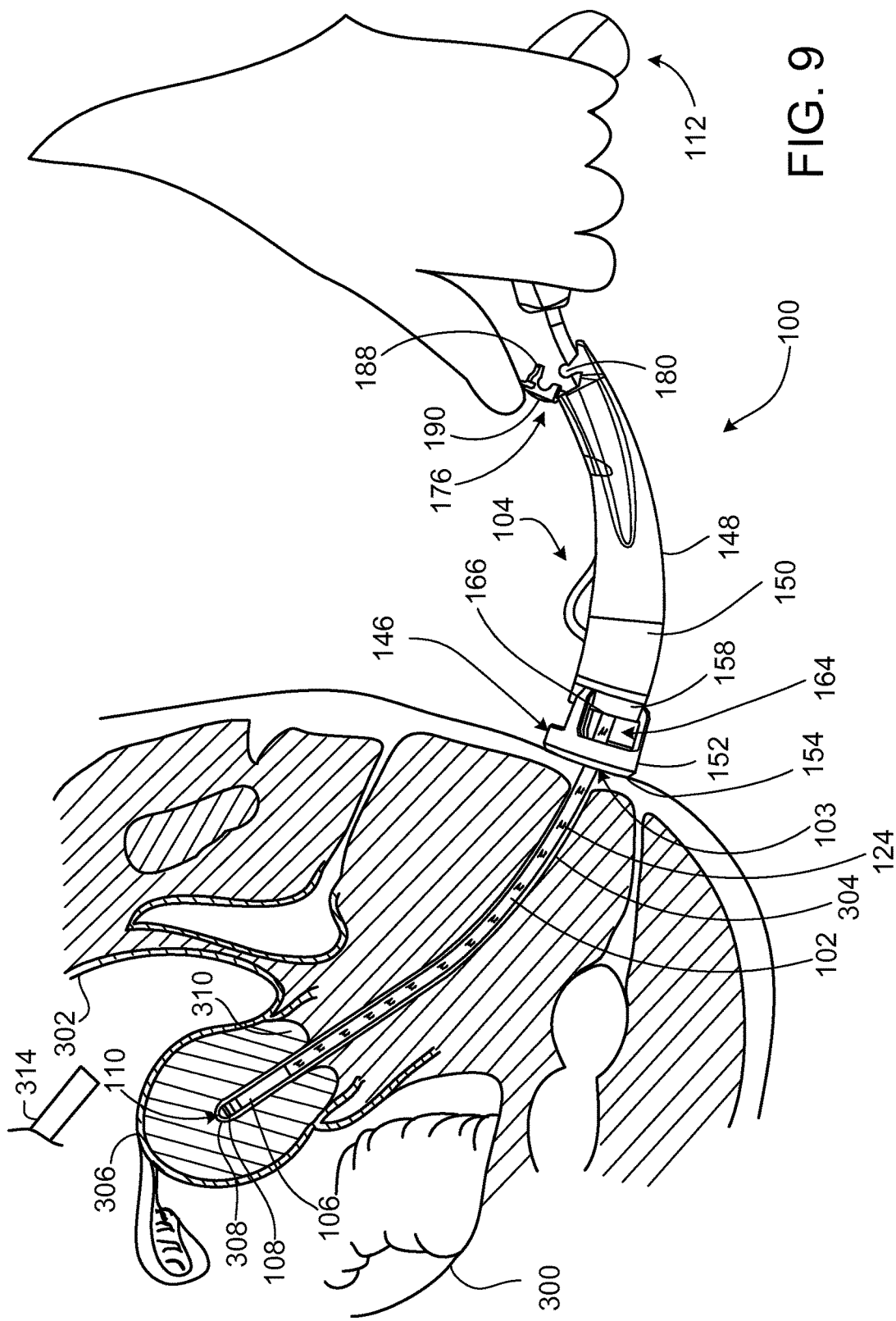
FIG. 9 is a cross-sectional side view of a pelvic cavity showing the uterine manipulator of FIG. 1 in a fully inserted position and with the colpotomizer assembly in a loading position.

As shown in FIG. 5, the vaginal occluder 150 includes a main body 194 that can be mounted concentrically about the distal cuff 196 of the sleeve 148, an expandable balloon cuff 198, and a balloon cuff catheter tube 101. The balloon cuff catheter tube 101 is affixed to the balloon cuff 198 and communicates fluid to the balloon cuff 198 when inflation is desired.

Figure 7:
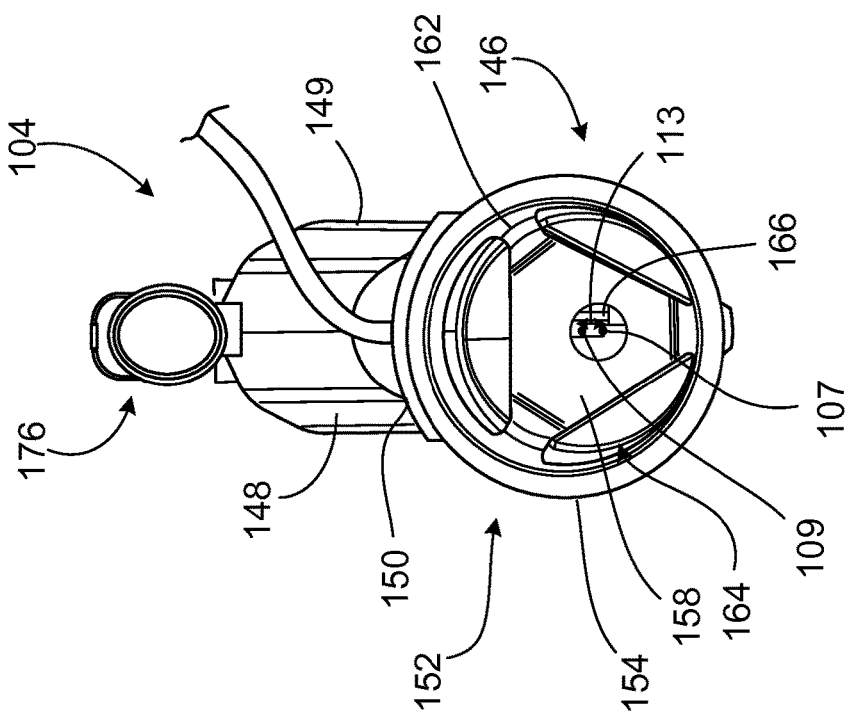
FIG. 7 is a front perspective view of the colpotomizer assembly of FIG. 1.

Referring to FIGS. 6 and 7, the colpotomizer assembly 104 of the uterine manipulator 100 has a geometry (e.g., provided by the position and size of the opening 166 of the base 158) that ensures proper alignment of the cup face 103 with respect to the shaft 102. The cup face 103 is oriented perpendicular (e.g., normal) to an axial centerline 109 of the colpotomizer cup 146. A centerpoint 105 of the cup face 103 (located along the axial centerline 109 of the colpotomizer cup 146) is maintained along an arch centerline 107 of the shaft 102 as the colpotomizer assembly 104 is slid along the shaft 102. Such alignment of the cup face 103 with the arch centerline 107 is provided by an offset 113 between the centerline 109 of the colpotomizer cup 146 and the arch centerline 107 of the shaft 102, at the location of the opening 166 of the base 158 of the colpotomizer cup 146. The offset 113 is typically a distance of about 0.065 inch to about 0.085 inch (e.g., about 0.071 inch to about 0.081 inch). The colpotomizer cup 146 is substantially prevented from tilting with respect to the shaft 102 by points of contact between the cup 146 and the shaft 102 at the opening 166 of the base 158 and the roller mount 182 and cam lock 184 of the thumb lock 176. Aligning the colpotomizer cup 146 with respect to the shaft 102 in this manner ensures that an appropriately angled cutting edge is achieved for guiding a cutting of the uterus with an even distribution of tissue when the cervix is received within the colpotomizer cup 146. In other words, this configuration can help to ensure that substantially the same amount of cervical tissue is received in the colpotomizer cup 146 about the entire circumference of the shaft 102, and can thus help to ensure that a symmetrical cut is made to the cervix during a surgical procedure, such as a hysterectomy.

The various components of the colpotomizer assembly 104 can be formed (e.g., molded and/or machined) from one or more materials that are biocompatible. In some embodiments, the colpotomizer cup 146 can be made of polyetherimide (PEI). In some embodiments, the female and male portions 168, 170 of the sleeve 148 can be made of acrylonitrile butadiene styrene (ABS). In some embodiments, certain components of the thumb lock 176 (e.g., the cam roller 184, the roller mount 186, the jaw 188, and the lift flange 192) can be made of polycarbonate. In some embodiments, the various components of the vaginal occluder 150 can be made of medical grade silicone. In some embodiments, the colpotomizer cup 146 and the sleeve 148 are formed (e.g., molded) as separate items that can then be connected together (e.g., via press fit or snap fit). This two-piece assembly can allow cup bodies of different sizes (e.g., different diameters) to be used with the same sleeve. While certain examples of materials with which the components of the colpotomizer assembly 104 can be formed have been described, it should be understood that other materials can alternately be used to form these components.

Referring to FIG. 8, in some embodiments, the uterine manipulator 100 is provided as a disposable (e.g., single-use) surgical device that is housed in a packaging container 200. The packaging container 200 provides an easy-to-open structure that allows for secure, space-saving transport and storage of the uterine manipulator 100. The packaging container 200 includes a base 202 that houses the uterine manipulator 100 and a cover 204 that can be peeled from the base 202 to open the packaging container 200. The base 202 of the packaging container 200 has a shape that generally follows the shape of the uterine manipulator 100. The base 202 of the packaging container 200 includes spaced apart posts 206 that secure the shaft 102 of uterine manipulator 100 in a stable position. The packaging container 200 can be transparent, translucent, or opaque and can be made of one or more materials that are biocompatible. For example, the packaging container 200 can be made of Ethylene-vinyl acetate.

The uterine manipulator 100 may be used in a number of procedures that require manipulation of the uterus, including surgical procedures, such as hysterectomies. In one example, the uterine manipulator 100 is used in a total laparoscopic hysterectomy (TLH) surgery. A patient is prepared for TLH surgery according to know procedures. Such procedures can include determining a depth of the uterus (e.g., as measured from the fundus of the uterus to the cervical os) using a sounding device or an ultrasound technique. For example, a sounding device that has ruler markings along its length may be inserted into the patient until a distal end is positioned adjacent the fundus of uterus according to visual confirmation of the depth reading at the cervix. The ruler marking located at the depth of the uterus (i.e., at the proximal end of the cervix) indicates the location where the colpotomizer cup 146 of the colpotomizer assembly 104 should be placed during the surgical procedure. In other words, the depth of the uterus corresponds to an operational position of the colpotomizer cup 146 for carrying out the procedure. As discussed above with respect to FIGS. 2-4, the ruler markings 124 along the shaft 102 of the uterine manipulator 100 indicate a distance from the fundus to the base 158 of the colpotomizer cup 146 when the uterine manipulator 100 is appropriately, fully inserted within the patient. The ruler markings 124 along the shaft 102 compensate for an arc length of the colpotomizer assembly 104, thereby reflecting an accurate depth placement of the colpotomizer cup 146. Proper placement of the uterine manipulator 100 with respect to the fundus, as aided by the lens 190 of the thumb lock 176 and the ruler markings 124 along the shaft 102, can prevent perforation and other damage to the fundus and the distal region of the uterus.

FIGS. 9-12 illustrate a method of using the uterine manipulator 100. Referring particularly to FIG. 8, once prepared, the patient's peritoneal cavity 300 is inflated with a gas (e.g., $CO_2$) to facilitate accessibility and visibility of the female pelvic organs and surgical instruments (e.g., a laparoscope 314) as the instruments are inserted through the abdominal wall 302 and into the peritoneal cavity 300. The colpotomizer assembly 104, while in an unlocked configuration, is slid proximally along the shaft 102 until the colpotomizer assembly 104 reaches a loading position (e.g., a position where the proximal end 174 of the sleeve 148 is positioned along the proximal portion 114 of the shaft 102). The button 119 located along the manipulator handle 112 for controlling the light source 110 is actuated (e.g., depressed or slid) to turn on the light source 110. Next, the uterine manipulator 100, with the colpotomizer assembly 104 in the loading position and with the light source 110 turned on, is inserted into the vaginal cavity 304. Light emitted from the light source 110 improves visibility of the vaginal cavity 304 as the uterine manipulator 100 is inserted. In some cases, the colpotomizer assembly 104 is locked in the loading position prior to insertion into the vaginal cavity 304. In other instances, the colpotomizer assembly 104 remains unlocked in the loading position during insertion into the vaginal cavity 304.

Figure 10:
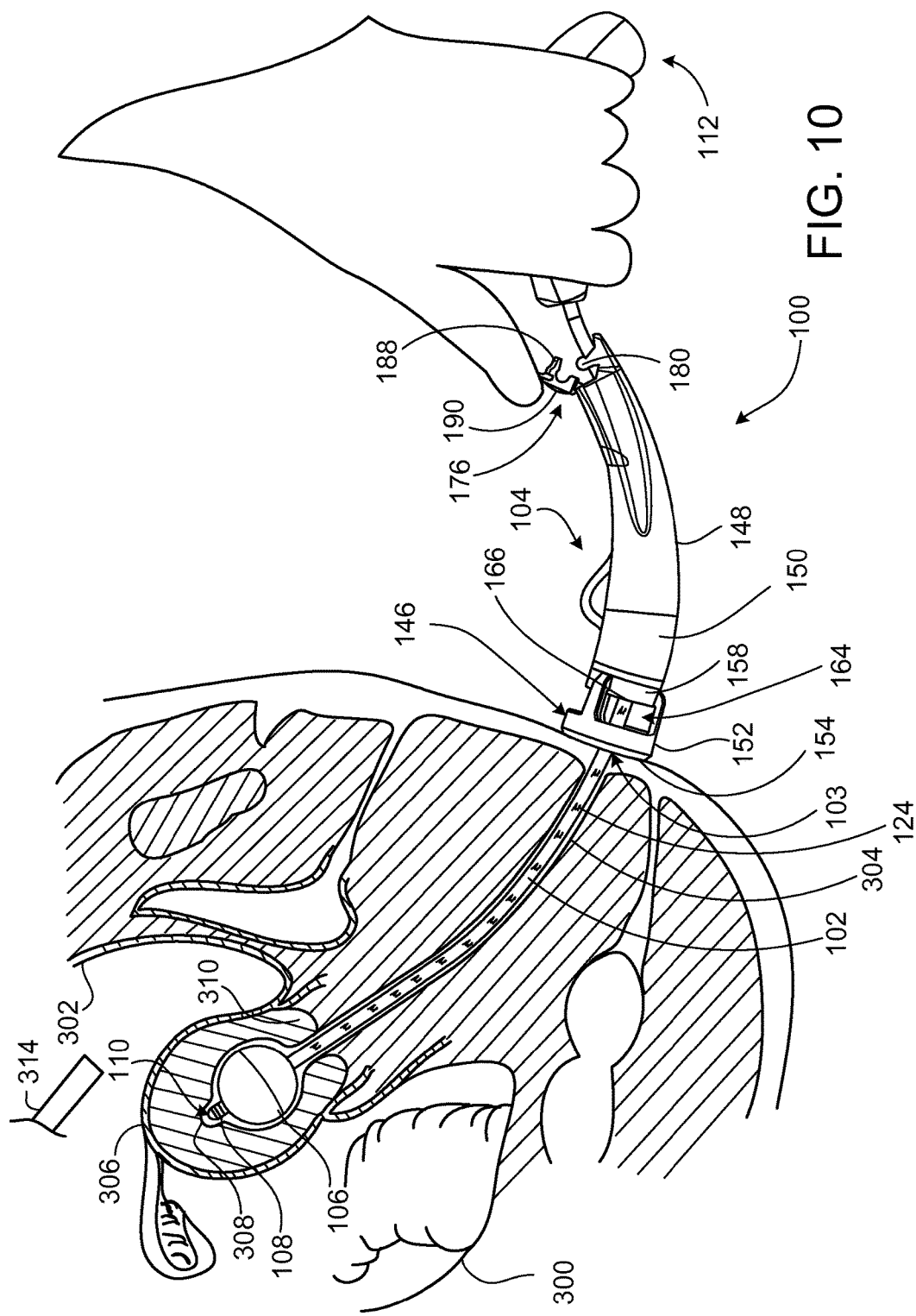
FIG. 10 is a cross-sectional side view of the pelvic cavity of FIG. 9, showing the uterine manipulator of FIG. 1 in a fully inserted position, with the expandable balloon inflated, and with the colpotomizer assembly unlocked in the loading position.

Referring to FIG. 10, the uterine manipulator 100 is moved distally within the vaginal cavity 304 until the distal tip 108 of the shaft 102 is positioned adjacent the fundus 308 of the uterus. The slidable button 144 of the syringe 138 is then slid distally (as shown in FIG. 2) to inflate the expandable balloon 106 such that the expandable balloon 106 engages an interior surface of the uterus 306. In some cases, the slidable button 144 may be slid proximally to deflate the expandable balloon 106 if it is determined that the uterine manipulator 100 needs to be repositioned. Leaving the colpotomizer assembly 104 in the loading position during insertion of the uterine manipulator 100 can allow for a relatively unobstructed view of the cervix 310 to help ensure proper placement of the distal tip 108 of the shaft 102.

Figure 11:
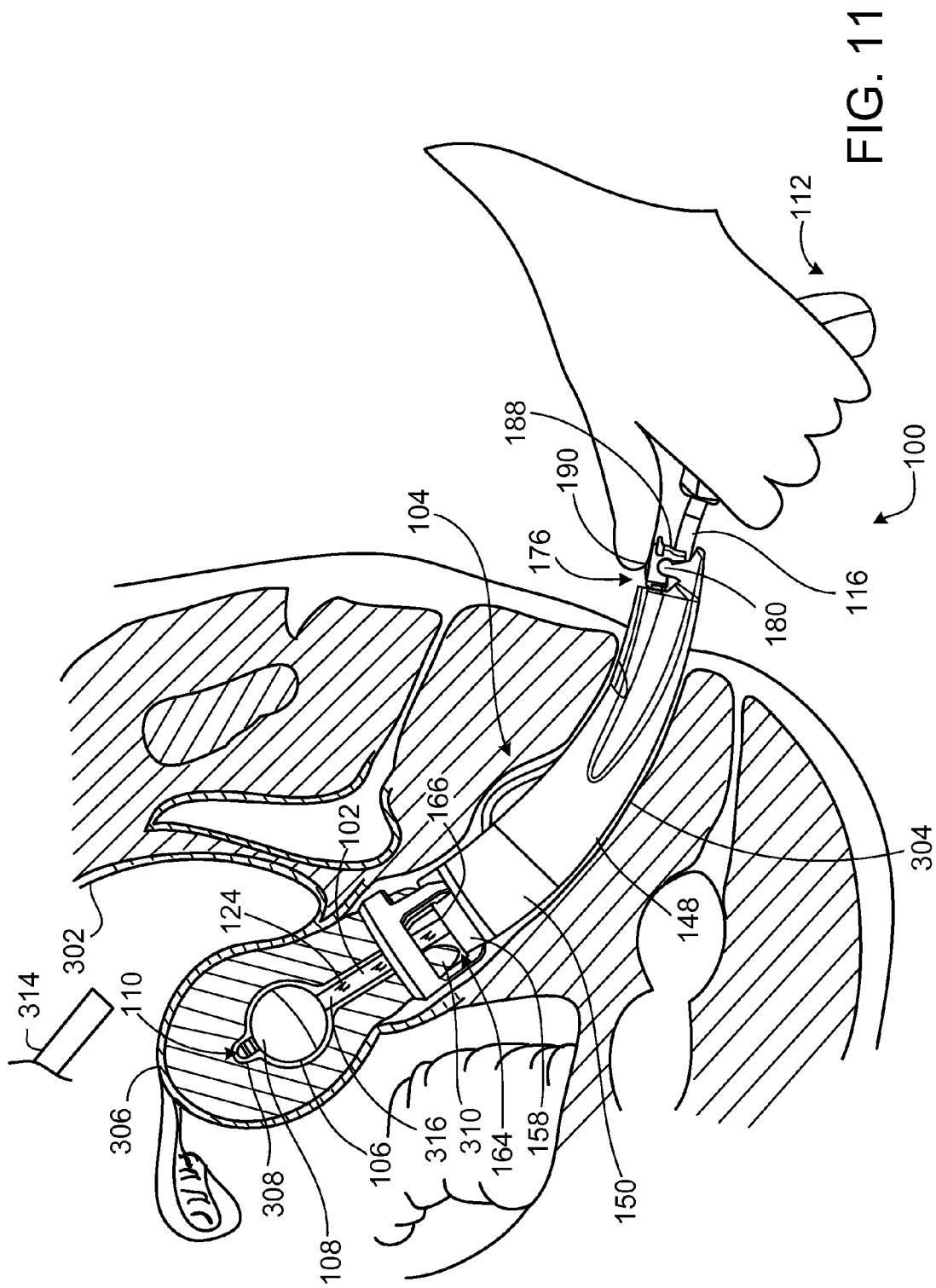
FIG. 11 is a cross-sectional side view of the pelvic cavity of FIG. 9, showing the uterine manipulator of FIG. 1 fully inserted, with the colpotomizer assembly locked in an operational position.

Referring to FIG. 11, the colpotomizer assembly 104 (still in the unlocked configuration) is advanced distally from the loading position until the ruler markings 124 (as visualized through the lens 190) indicate that the base 158 of the colpotomizer cup 146 is positioned at an operational position (i.e., at a distance from the distal tip 108 that is approximately equal to the depth of the uterus 306 as determined from the sounding device). The viewing windows 164 of the colpotomizer cup 146 can provide for additional visual confirmation of placement. In the operational position, the cervix 310 is positioned within the body 152 of the colpotomizer cup 146 and abuts the base 158 of the colpotomizer cup 146. The alignment of the lens 190 with the ruler marking 124 and the ability to view placement of the cervix 310 within the colpotomizer cup 146 through the viewing windows 164 helps to ensure that the colpotomizer cup 146 is fully forward in the desired position relative to the distal tip 108 of the shaft 102 and relative to the cervix 310. In this position, the colpotomizer cup 146 provides an anatomical landmark at the base of the uterus 306 (e.g., indicating a location of an apex of the cervix 310) and an incision backstop (e.g., an edge that defines where the uterus 306 should be cut). Furthermore, the cup face 103 of the colpotomizer cup 146 is centered on the arch centerline 107 of the shaft 102, ensuring a proper angular position of the colpotomizer cup 146 with respect to the shaft 102 for providing a desirable or suitable cutting guide.

With the colpotomizer assembly 104 positioned as desired, the jaw 188 of the thumb lock 176 is then depressed to lock the colpotomizer assembly 104 at the operational position. The jaw 188 can be depressed using the same hand that advances the colpotomizer assembly 104 within the vaginal cavity 304, such that distal movement and locking of the colpotomizer assembly 104 can be performed in a one-handed operation. If necessary, the lift flange 192 of the thumb lock 176 can be pushed upwards to unlock the colpotomizer assembly 104 for repositioning along the shaft 102. In some implementations, the mechanical integrity of the thumb lock 176 may be maintained over multiple (e.g., four) lock-unlock cycles.

Figure 12:
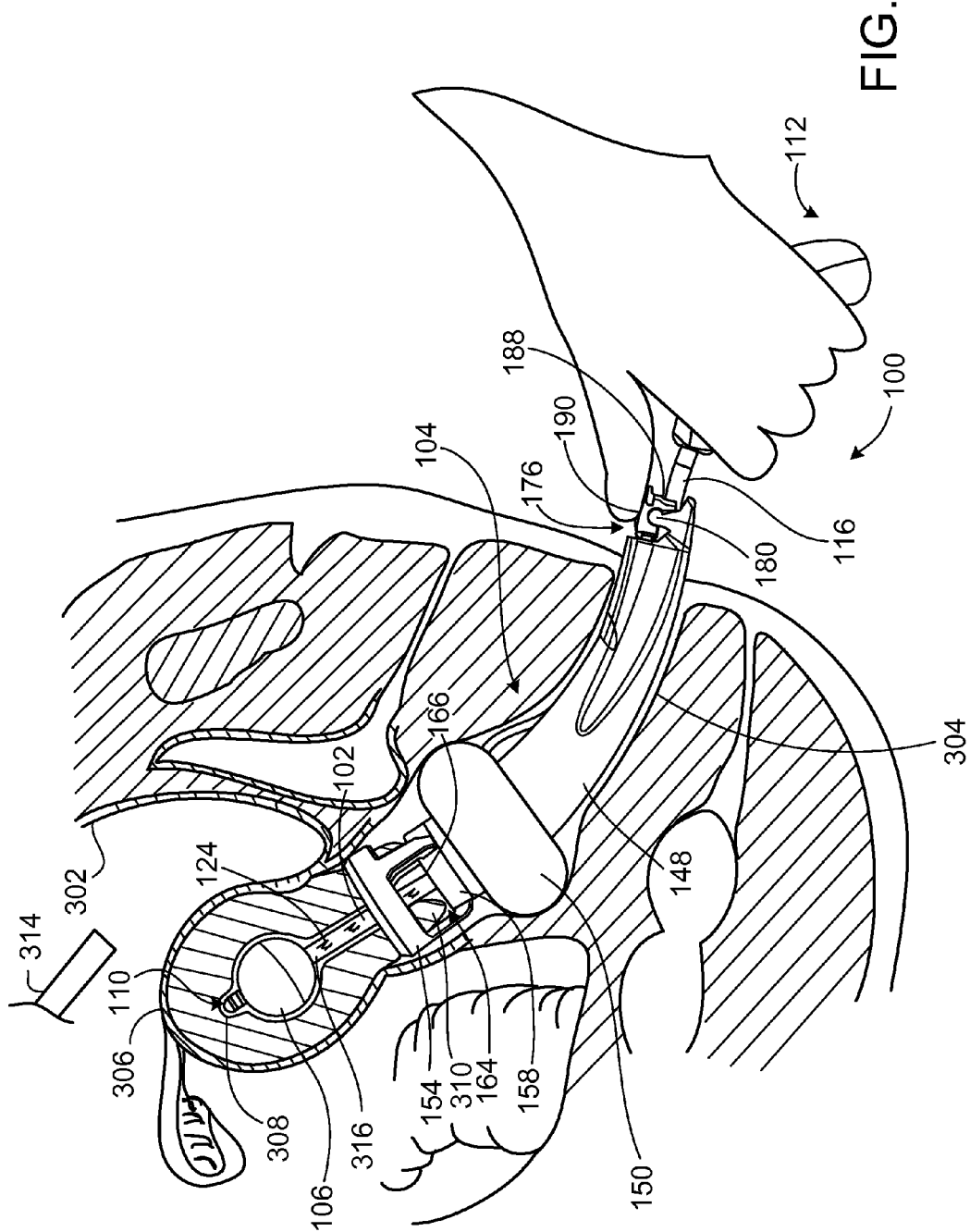
FIG. 12 is a cross-sectional side view of the pelvic cavity of FIG. 9, showing the uterine manipulator of FIG. 1 supporting a uterus.

Referring to FIG. 12, once the colpotomizer assembly 104 is locked in the desired operational position along the shaft 102, the vaginal occluder 150 can be inflated (e.g., with a sterile, water-based fluid) to seal a distal region of the vaginal cavity 304, thereby maintaining pneumoperitoneum. The vaginal occluder 150 inhibits (e.g., prevents) the escape of gas used to inflate the peritoneal cavity 300 during and following the first of any colpotomy incisions.

A surgeon can then manipulate or move the uterus 306 into a desired position to perform surgical procedures that include cutting around the base of the uterus 306. As discussed above, the offset 113 (located at the opening 166 in the base 158 of the colpotomizer cup 146) between the centerline 109 of the colpotomizer cup 146 and the arch centerline 107 of the shaft 102 ensures that the centerpoint 105 of the cup face 103 is located along the arch centerline 107 of the shaft 102. Such a configuration prevents undesired tilting of the colpotomizer cup 146 relative to the shaft 102, such that cutting along the cup face 103 results in a symmetrical cut of the uterus 306 with an even distribution of tissue within the colpotomizer cup 146. After the uterus 306 is completely incised such that the uterus 306 is totally free in the peritoneal cavity 300 and held only by the uterine manipulator 100, then the uterine manipulator 100, along with the supported uterus 306, is removed through the vaginal cavity 304. The uterine manipulator 100 can be disposed of following the surgery.

While certain embodiments have been described above, other embodiments are possible.

For example, while the locking mechanism of the colpotomizer assembly 104 is described as being located at the proximal end 174 of the sleeve 148, in other embodiments, a locking mechanism may be located a different location (e.g., at an intermediate location) along a length of a colpotomizer assembly.

While a specific configuration of a one-handed cam-based locking mechanism has been described, other types of locking mechanisms can be used. In certain embodiments, for example, a uterine manipulator may include a different type of one-handed cam-based locking mechanism. Such example locking mechanisms may include a screen door mechanism, a Touhy Borst mechanism, or a sheet metal skive capture mechanism.

While the colpotomizer assembly 104 has been described as including a one-handed locking mechanism, in some embodiments, a uterine manipulator may include a colpotomizer assembly that has a two-handed locking mechanism.

While the uterine manipulator 100 has been described as including the integral syringe 138, in some embodiments, a uterine manipulator may not include an integral syringe. For example, in some embodiments, a syringe may alternatively be secured externally to a proximal end of a manipulator handle of a uterine manipulator.

While the uterine manipulator 100 has been described as including the integrated light source 110, in some embodiments, a uterine manipulator may not include an integrated light source. For example, in some embodiments, a uterine manipulator may be used with a separate or external light source. In other examples, a uterine manipulator may be used without a light source.

While the uterine manipulator 100 has been described as disposable, in some embodiments, the uterine manipulator 100 may be reusable (e.g., sterilizable).

What is claimed is:

1. A uterine manipulator, comprising:
   an arcuate shaft configured to be inserted into a cervix; and
   a colpotomizer assembly configured to move along the arcuate shaft, the colpotomizer assembly comprising a cup configured to receive the cervix, the cup defining:
   a cup face disposed substantially perpendicular to an axial centerline of the cup and having a centerpoint disposed along the axial centerline of the cup, and
   an opening through which the arcuate shaft passes, the opening spaced apart from the cup face such that an arcuate centerline of the arcuate shaft is aligned with the centerpoint of the cup face, and such that the arcuate centerline of the arcuate shaft is offset from the axial centerline of the cup at the opening.

2. The uterine manipulator of claim 1, wherein the arcuate shaft comprises a proximal portion, a central portion along which the colpotomizer assembly can move, and a distal tip.

3. The uterine manipulator of claim 1, wherein the arcuate shaft is a rigid shaft.

4. The uterine manipulator of claim 1, wherein the cup comprises a cup body that defines the cup face at a distal end of the cup.

5. The uterine manipulator of claim 4, wherein the cup body is configured to receive the cervix.

6. The uterine manipulator of claim 4, wherein the cup body defines a plurality of viewing windows for visualizing the cervix within the cup body.

7. The uterine manipulator of claim 4, wherein the cup body defines a beveled rim configured to provide an anatomical landmark and an incision backstop.

8. The uterine manipulator of claim 1, wherein the cup comprises a base defining the opening.

9. The uterine manipulator of claim 1, wherein the arcuate centerline of the arcuate shaft is offset by about 0.065 inch to about 0.085 inch from the axial centerline of the cup at the opening.

10. The uterine manipulator of claim 1, wherein the colpotomizer assembly further comprises a sleeve connected to the cup and defining a channel configured to receive the arcuate shaft.

11. The uterine manipulator of claim 10, wherein the sleeve comprises a locking member configured to lock the colpotomizer assembly at any of a plurality of different locations along the arcuate shaft.

12. The uterine manipulator of claim 10, wherein the colpotomizer assembly further comprises a vaginal occluder.

13. The uterine manipulator of claim 1, further comprising a manipulator handle secured to the arcuate shaft.

14. The uterine manipulator of claim 13, wherein the manipulator handle comprises an integrated syringe configured to displace air within a central lumen of the arcuate shaft.

15. The uterine manipulator of claim 14, further comprising an expandable balloon disposed along a distal tip of the arcuate shaft and in fluid communication with the central lumen of the arcuate shaft.

16. The uterine manipulator of claim 15, wherein the integrated syringe is configured to deliver air to and withdraw air from the expandable balloon.

17. The uterine manipulator of claim 13, further comprising an integrated light source mounted to a distal tip of the arcuate shaft.

18. The uterine manipulator of claim 17, wherein the manipulator handle comprises a power source for powering the integrated light source.

19. The uterine manipulator of claim 1, wherein the uterine manipulator is a single-use device.

20. The uterine manipulator of claim 1, further comprising a shrink tube disposed about the arcuate shaft for facilitating movement of the colpotomizer assembly along the arcuate shaft and locking of the colpotomizer assembly along the shaft.

21. The uterine manipulator of claim 1, wherein the arcuate centerline of the arcuate shaft remains aligned with the centerpoint of the cup face as the colpotomizer assembly is moved along the arcuate shaft.

22. The uterine manipulator of claim 21, wherein the cup is prevented from tilting with respect to the arcuate centerline of the arcuate shaft as the colpotomizer assembly is moved along the arcuate shaft.

23. The uterine manipulator of claim 1, wherein the opening of the cup is radially spaced from the axial centerline of the cup.

* * * * *